US00PP12019P2

(12) United States Plant Patent
Sherman

(10) Patent No.: US PP12,019 P2
(45) Date of Patent: Jul. 31, 2001

(54) 'UF2000' PEACH TREE

(76) Inventor: Wayne B. Sherman, University of Florida, P.O. Box 110690, Gainesville, FL (US) 32611-0690

( * ) Notice: Subject to any disclaimer, the term of this patent is extended or adjusted under 35 U.S.C. 154(b) by 0 days.

(21) Appl. No.: 09/376,682

(22) Filed: Aug. 18, 1999

(51) Int. Cl.[7] ..... A01H 5/00
(52) U.S. Cl. ..... Plt./197
(58) Field of Search ..... Plt./197

*Primary Examiner*—Bruce R. Campbell
*Assistant Examiner*—Susan B. McCormick

(57) ABSTRACT

A new and distinct variety of peach tree which has a low winter chilling requirement of approximately 300 chill units (cu). The tree is of large size, is highly vigorous with a semi upright growth habit and has showy pink flowers. Glands are small and reniform in shape and isolated to the basal portions of leaves. This tree, which has been denominated 'UF2000' is a regular bearer of heavy crops which are large for the moderately early ripening season, with yellow and very firm non-melting flesh, clingstone fruit. Fruit are uniform, attractive, substantially symmetrical shape, and have an attractive normally 50 to 70% solid red skin. The fruit ripens 15 to 18 days after 'UFGold' in mid-to late May at Gainesville.

1 Drawing Sheet

BACKGROUND OF THE NEW VARIETY

The present invention relates to a new and distinct variety of peach (*Prunus persica* (L.) Batsch) tree which is named 'UF2000' and, more particularly to a peach tree which produces highly colored, good eating quality, clingstone, non-melting flesh fruit which are mature for fresh market in mid-to late May at Gainesville and are produced on a tree adapted to a mild winter climate. Asexual propagation was performed at Gainesville, Fla. where the selection was made and trees were tested. Contrast is made to 'UFGold' (U.S. Plant Pat. No. 10,315) peach, a standard variety, for reliable description. This new variety is a promising candidate for commercial success in that it retains fruit firmness at the full flavor, tree ripe stage for 10 days on the tree.

ORIGIN OF THE VARIETY

This peach tree (genotype) originated in the fruit breeding program at the University of Florida, located at Gainesville, Fla. The seed parent was 'Aztecgold' (nonpatented), a non-melting flesh peach (originated as an $F_2$ of 'Sunred' nectarine×'Mexican Cling' peach). The pollen parent was 'Oro A' (nonpatened), a non-melting flesh peach that originated as a seed importation from Brazil. 'UF2000' ripens mid to late May, between 'Aztecgold' (early June) and 'Oro A' (early May). 'UF2000' peach was selected from about 150 sibs as the $15^{th}$ selection in 1992, and exhibited yellow, non-melting, clingstone flesh, and was designated Fla. 92-15C. It was propagated as a uniform variety through two successive standard asexual propagation by budding on 'Flordaguard' (nonpatented) seedling rootstock (for root-knot nematode control) and determined at Gainesville to have unique tree and fruit characteristics making it worthy for commercial fresh fruit production. There are no known effects of this rootstock on this scion cultivar.

SUMMARY OF THE VARIETY

The new and distinct variety of peach tree bears yellow, non-melting flesh fruit, and has a moderate-chilling dormancy requirement. 'UF2000' blooms about 10 days after 'UFGold' peach at Gainesville, bearing red skin, non-melting and yellow flesh fruit. The estimated chilling requirement is 300 chill units.

The present invention resulting in 'UF2000' peach tree is characterized by non-melting flesh fruit of excellent flavor and eating quality on a tree adapted to mild winters. The trees are vigorous, productive and regular bearing. Trees attain in two years, a height of three meters and a spread of two meters at Gainesville. Terminal growth of up to a meter annually is common on mature five-year-old trees with normal pruning to a vase shape. The first fruit ripen in mid-to late May at Gainesville or in about 95 days from full bloom which is about 15 to 18 days after 'UFGold'. The fruit are uniformly large for an early peach. Ripe fruit have 50 to 70% of solid (no stripes) red skin with no red pigment in the flesh at the pit, but have some red pigment in the outer flesh on the sun exposed side of the fruit. The flower anthers are light red to yellow, a common characteristic of many standard peach and nectarine varieties.

BRIEF DESCRIPTION OF THE DRAWING

The accompanying drawing is a color photograph which shows a typical specimen of the fruit, leaf, and stem of the new variety as nearly true as it is reasonably possible to make in a color illustration of this type. The photograph shows an attractive shape and exterior coloration of four specimens of fruit above a ruler in side view, stem end view, a blossom end view, and side view showing the suture.

DETAILED BOTANICAL DESCRIPTION

The tree, flowers, and fruit may vary in slight detail due to variations in soil type, cultural practices, and climatic condition. The potential for commercial production of fresh fruit by 'UF2000' is high, due to its attractive red skin, early ripening, good flavor, and exceptional firmness due to its non-melting flesh. The present botanical description is that of the variety grown under the ecological conditions prevailing at Gainesville, Fla. Colors are described from "The Pantone Book of Color" published by H. N. Abrams, Inc., N.Y. 1990.

Tree:

*Size.*—Trees are large when trained to an open vase form.

*Vigor.*—Highly vigorous, and must be summer and winter pruned to keep tree height restricted and to keep center of vase open.

*Density.*—Medium to dense in branching habit.

*Form.*—Semi-upright when pruned to vase shape.

*Bearer.*—Very productive and self fertile, must be fruit thinned to avoid limb breakage and obtain desired fruit size.

Trunk:

*Size.*—Medium trunk diameter attaining 10 cm diameter at a height of 30 cm at the end of 3 years growth at Gainesville.

*Texture.*—Medium smooth, but changes to medium rough as tree ages.

*Bark color.*—Older bark — Lead Gray (Pantone 17-1118).

*Lenticels.*—Numerous, small (2–4 mm), and flatoral (while slightly raised, lenticels are flat across the top) shape, with the center being Mineral Yellow (Pantone 15-1046).

Branches:

*Size.*—Vigorous growth of scaffold branches.

*Texture.*—Relatively smooth, medium amount of lenticels attaining size found on trunk and old scaffolds.

*Color.*—New wood, Tarragon (Pantone 15-0326); Old wood, Lead Gray (Pantone 17-1118).

Leaves:

*Size.*—Medium; 15 to 19 cm length, including the petiole; 3 to 4 cm width. Measurements on vigorous upright shoots of summer growth.

*Thickness.*—Regular and average for commercial peach varieties.

*Form.*—Lanceolate.

*Apex.*—Acute.

*Margin.*—Serrulate, slightly undulate.

*Base.*—Cuneate.

*Surface.*—Upper, glabrous; Lower, medium large veins.

*Color.*—Lower-Grasshopper (Pantone 18-0332); Upper-Black Forest (Pantone 19-0315).

*Glands.*—Two to four small reniform glands mostly on lower leaf blade, but occasionally on petiole.

*Petiole.*—About 1 cm (0.7 to 1.1 cm).

*Stipules.*—Medium (equal that of most commercial peach varieties) and early deciduous.

*Arrangement.*—Alternate.

Flower buds:

*Abundance.*—Moderately high, most buds set fruit in absence of spring frosts.

*Size.*—Medium, average 3.5 mm length.

*Form.*—Plump, conic.

*Surface.*—Pubescent scales.

*Color.*—Stucco, (Pantone 16-1412) in late winter.

Flowers:

*Blossom period.*—10 days after 'UFGold' peach — average February 12–16 at Gainesville.

*Aroma.*—Slight to none as is typical of most peaches grown for commercial fruit.

*Type.*—Showy, location and seasonably variable 42 mm average diameter, but within the midrange size of showy flower. Petal length, 18 mm average; width, 11 mm average. Petal texture — smooth.

*Color.*—Candy Pink (Pantone 14-1911) when first open, darkening to Aurora Pink (Pantone 15-2217) near flower center and fading to Orchid Pink (Pantone 13-2010) in outer portion before abscising. Upper and lower surface similar color.

*Calyx cup.*—Medium small as compared to commercial varieties.

*Anthers.*—Light red to yellow, Jaffa Orange (Pantone 16-1454) darkest when flowers begin opening and fading before pollen is shed, regular size. Size is not uniquely different than that of most self fertile peach varieties.

*Pollen.*—Abundant and bright yellow Snapdragon (Pantone 13-0840) (common to many varieties).

*Fertility.*—Self fertile.

Fruit:

*Maturity when described.*—Tree-ripe, May 18, 1998 at Gainesville.

*Date of first picking.*—May 18, 1998 at Gainesville (normal).

*Date of last picking.*—May 27, 1998 at Gainesville.

*Size.*—Uniform, medium large (large size for early maturity at 140 to 160 grams).

*Average diameter axially.*—2½ inches (63 mm).

*Average length.*—2⅝ inches (65 mm).

*Pubescence.*—Medium, longer than for 'UFGold', not visually different than 'Aztecgold'.

*Stem length.*—Medium in size: Length — approximately 5/16 inch; Width — approximately ⅛ inch.

Form:

*Longitudinal section form.*—Slightly oval.

*Transverse section through diameter.*—Round.

*Suture.*—Shallow and inconspicuous.

*Ventral surface.*—Rounded.

*Base.*—Slightly retuse.

*Apex.*—Round to slight point.

*Cavity.*—Flaring circular.

*Cavity depth.*—¼ to ⅜ inch (6 to 9 mm).

*Cavity breadth.*—5/32 inch (3 mm).

Skin:

*Thickness.*—Medium in comparison to commercial peach varieties.

*Texture.*—Medium in comparison to commercial peach varieties.

*Tenacity.*—Tenacious to flesh.

*Color.*—Paprika (Pantone 17-1553) over 50 to 70% of skin. Ground color is Sun Orange (Pantone 16-1257).

*Tendency to crack.*—None observed.

Flesh:

*Ripens.*—Evenly within each fruit and throughout the tree.

*Texture.*—Firm, juicy, non-melting when fully ripe.

*Fibers.*—Very fine, tender, small.

*Aroma.*—Moderate and in the middle range of commercial peach varieties.

*Eating quality.*—Good, sweet, subacid.

*Juice.*—Abundant.

*Color.*—Banana (Pantone 13-0947) with no redness at pit.

*Browning by oxidation.*—Slight on soft ripe fruit.

*Amygdalin.*—Undetected by taste.

Stone:

*Type.*—Clingstone, adhering to flesh even at softening.

*Size.*—Medium small; average length — 30 mm, average width — 23 mm.

*Color.*—Gold Earth (Pantone 15-1234 ) when freshly exposed.

*Form.*—Oblong.

*Base.*—Straight.

*Apex.*—Acute.

*Sides.*—Near equal.

*Surface.*—Irregularly furrowed toward the ventral edge.

*Ridges.*—Jagged toward the base.

*Pit wall.*—3/16 to ¼ inch thick (5 to 6 mm).

*Tendency to split.*—None observed.

Use: Fresh; dessert.

Resistance to disease: High resistance to bacterial spot incited by *Xanthomonas campestris* pv. *pruni* (Smith)Dye and retains leaves better than most standard varieties in late autumn when infected by rust incited by *Tranzschslia pruni-spinosae* (*pers*)*Diet.*

Keeping quality: Excellent after 2 weeks at 35F.

Shipping quality: Degree of firmness at harvest and firmness retained in refrigeration indicates fruit should be highly acceptable for shipping.

We claim:

1. A new and distinct peach tree variety as illustrated and described, characterized by a low-chilling requirement, and bearing early-ripening fruit with firm, yellow, non-melting flesh of high eating quality and an attractive, high percentage red overcolor with fruit ripening in mid-to late May or 15 to 18 days after 'UFGold' at Gainesville, Fla.

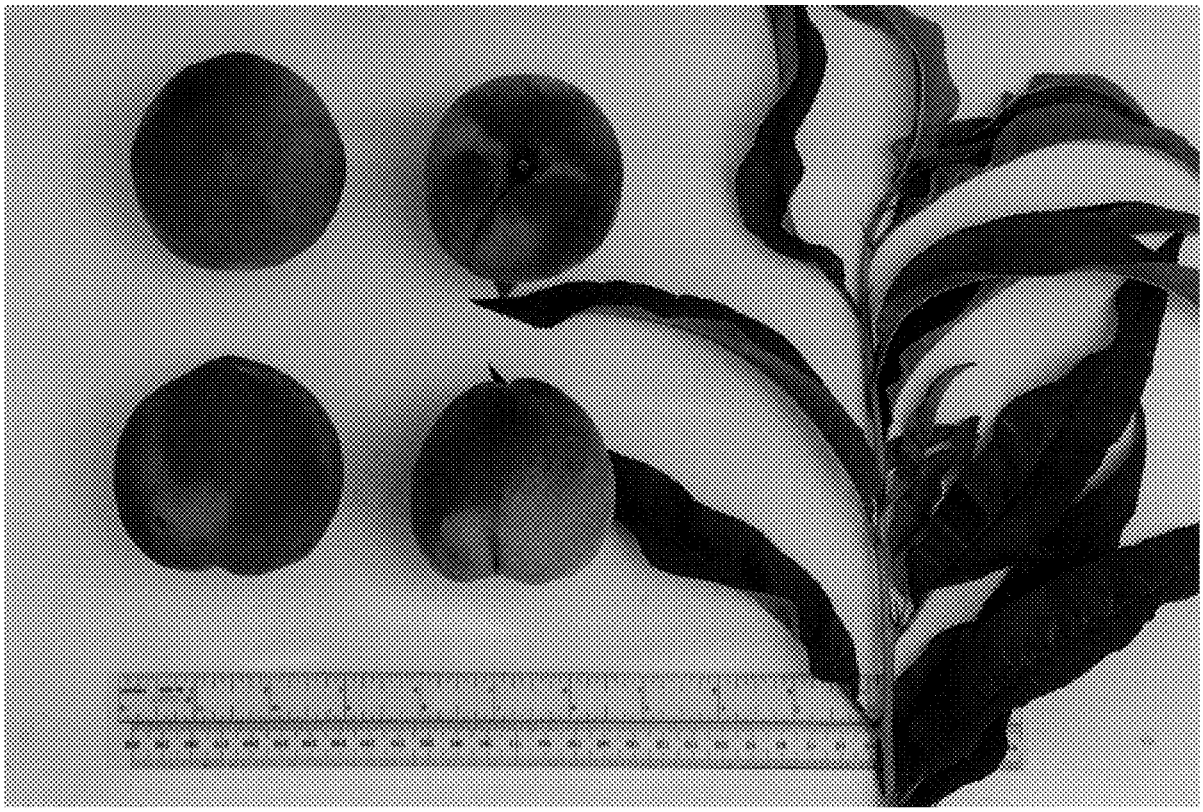

* * * * *